United States Patent [19]
Guracar et al.

[11] Patent Number: 5,961,460
[45] Date of Patent: Oct. 5, 1999

[54] ULTRASOUND IMAGING ENHANCEMENT METHODS AND SYSTEMS

[75] Inventors: Ismayil Guracar, Redwood City; Gregory Holley, Mountian View; Ting-Lan Ji; Bhaskar Ramamurthy, both of San Jose, all of Calif.

[73] Assignee: Acuson Corporation, Mountain View, Calif.

[21] Appl. No.: 08/838,920

[22] Filed: Apr. 11, 1997

[51] Int. Cl.$^6$ ........................................ A61B 8/00
[52] U.S. Cl. ........................ 600/440; 600/441; 600/458
[58] Field of Search ................................ 600/440, 441, 600/443, 447, 458; 367/7

[56] References Cited

U.S. PATENT DOCUMENTS

| | | |
|---|---|---|
| 4,712,037 | 12/1987 | Verbeek et al. . |
| 5,034,931 | 7/1991 | Wells ........................................ 367/126 |
| 5,111,823 | 5/1992 | Cohen . |
| 5,115,809 | 5/1992 | Saitoh et al. . |
| 5,215,094 | 6/1993 | Franklin et al. ........................ 600/458 X |
| 5,255,683 | 10/1993 | Monaghan . |
| 5,287,753 | 2/1994 | Routh et al. . |
| 5,301,670 | 4/1994 | Sato et al. ................................ 600/454 |
| 5,313,948 | 5/1994 | Murashita et al. . |
| 5,358,466 | 10/1994 | Aida et al. . |
| 5,396,285 | 3/1995 | Hedberg et al. . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,469,850 | 11/1995 | Sasabi et al. ............................ 600/443 |
| 5,471,990 | 12/1995 | Thirsk . |
| 5,476,097 | 12/1995 | Robinson ................................ 600/441 |
| 5,479,926 | 1/1996 | Ustuner et al. . |
| 5,526,816 | 6/1996 | Arditi . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,601,086 | 2/1997 | Pretlow, III et al. . |
| 5,617,862 | 4/1997 | Cole et al. . |
| 5,628,322 | 5/1997 | Mine . |
| 5,632,277 | 5/1997 | Chapman et al. . |
| 5,720,291 | 2/1998 | Schwartz . |
| 5,724,976 | 3/1998 | Mine . |
| 5,833,613 | 11/1998 | Arerkiou et al. ........................ 600/440 |

FOREIGN PATENT DOCUMENTS

| | | |
|---|---|---|
| 0 357 164 | of 0000 | European Pat. Off. . |
| 0 770 352 A1 | 5/1997 | European Pat. Off. . |
| 8-294487 | 11/1996 | Japan ........................................ 600/458 |
| WO 98/20361 | 5/1998 | WIPO . |

OTHER PUBLICATIONS

Williams, A. "UTS Imaging Technique Using Non–Linear Scattering From Buffles" WO 91/15999 Intnl Publication Oct. 31, 1991 Pub. Date.

Averkiou, M. et al "UTS Diagnostic Imaging of Response Frequency Differing from Transit Frequency" EP 0851241 A2 Publ. Jul. 1, 1998.

(List continued on next page.)

*Primary Examiner*—Francis J. Jaworski
*Attorney, Agent, or Firm*—Brinks Hofer Gilson & Lione

[57] ABSTRACT

An ultrasonic imaging system generates Doppler and B-mode image signals, and then uses a modulated, non-linear mapping function to combine the Doppler and B-mode image signals into an output signal. In another mode of operation the imaging system generates fundamental and harmonic frequency intensity values and maps these intensity values to display indicia, preferably with a modulated, non-linear mapping function.

68 Claims, 6 Drawing Sheets

OTHER PUBLICATIONS

Deborah J. Rubens, M.D., "Sonoelasticity Imaging of Prostate Cancer: In Vitro Results." Radiology, vol. 195, No. 2, 1995.

Fred Lee, Jr., M.D., "Sonoelasticity Imaging: Results in in Vitro Tissue Specimens." Radiology, vol. 181, No. 1 Oct. 1991.

Kevin J. Parker, PhD, et al., "Sonoelasticity of Organs: Shear Waves Ring a Bell." J. Ultrasound Med. 11 (1992).

Nico de Jong, "Physical properties and technical aspects of ultrasound contrast agents."

Robert M. Lerner, et al., "Sonoelasticity' Images Derived from Ultrasound Signals in Mechanically Vibrated Tissues." Ultrasound in Med. and Biol., vol. 16, No. 3, 1990.

J. Ophir, et al., "Elastography: A Quantitative Method for Imaging the Elasticity of Biological Tissues." Ultrasonic Imaging 13, (1991).

J.A. Hossack, et al., "Improving transducer performance using multiple active layers." SPIE vol. 1733 (1992).

Vokmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

"HP Ultrasound Technologies—Viability." About HP Ultrasound Imaging, WWW document 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology." American College of Cardiology, $45^{th}$ Annual Scientific Session, Mar. 24–27, 1996 pp. 21A, 63A, 239–240A.

Yang–Sub Lee, et al., "Time–domain modeling of pulsed finite–amplitude sound beams." J. Acoustical Society of America, 97 (2), Feb. 1995.

Michalakis A. Averkiou, et al. "Self–demodulation of amplitude and frequency. Modulated pulses in a thermouisceus fluid", J. Acoustical Society of America, vol. 94, No. 5, Nov. 1993.

Powers, J.E. et al "UTS Diagnostic Imaging w/Contrast Agents" EP 0770352 Publ. May 2, 1997.

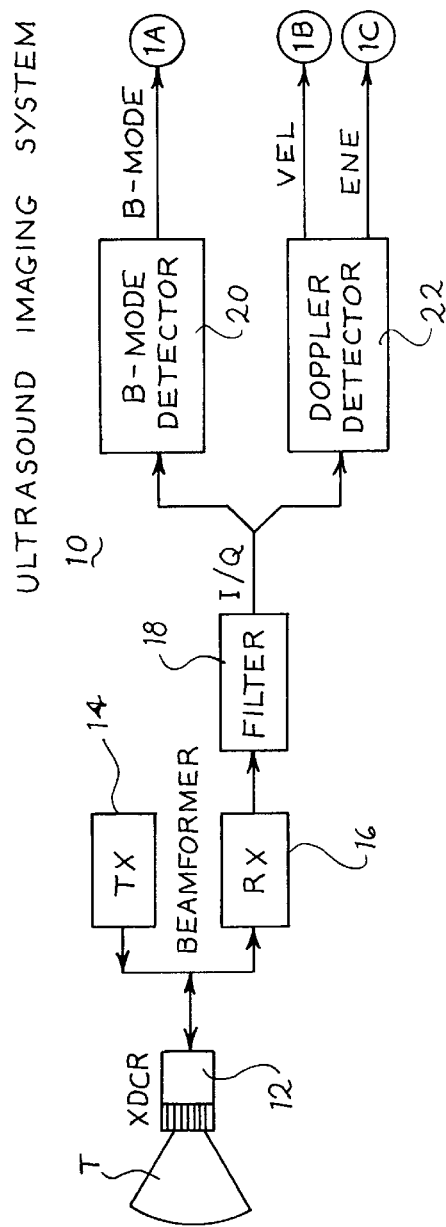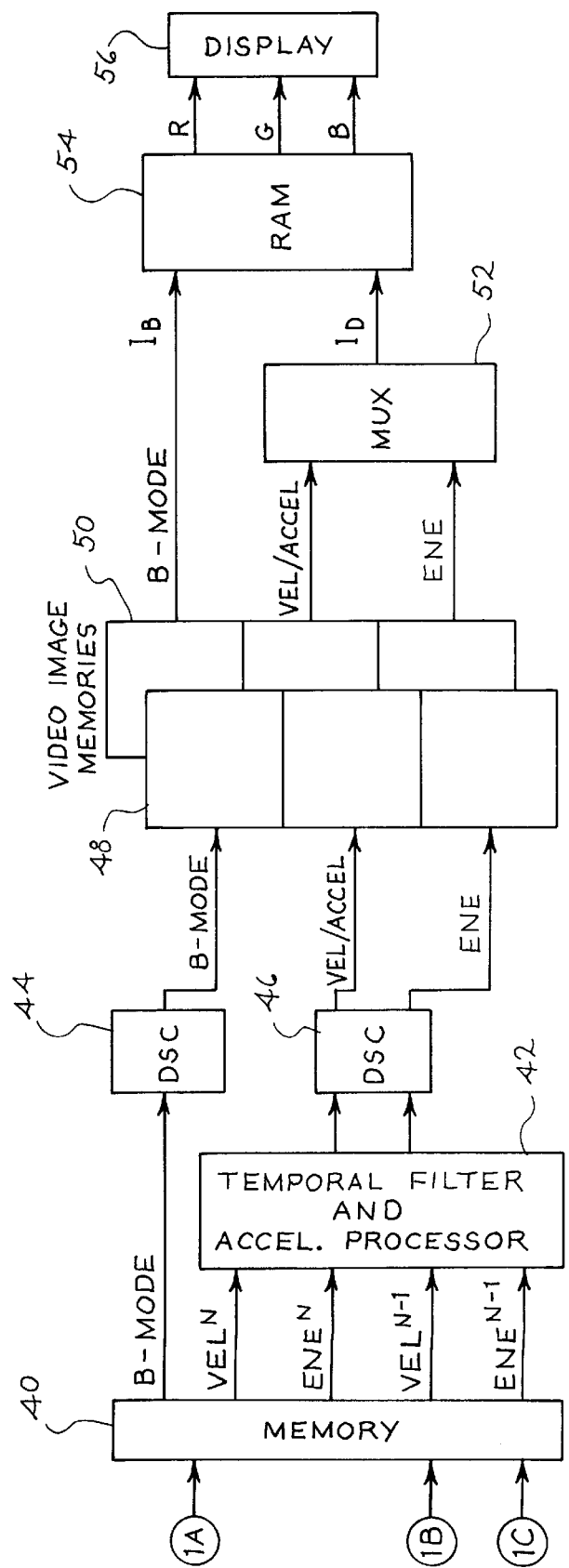
Fig. 1

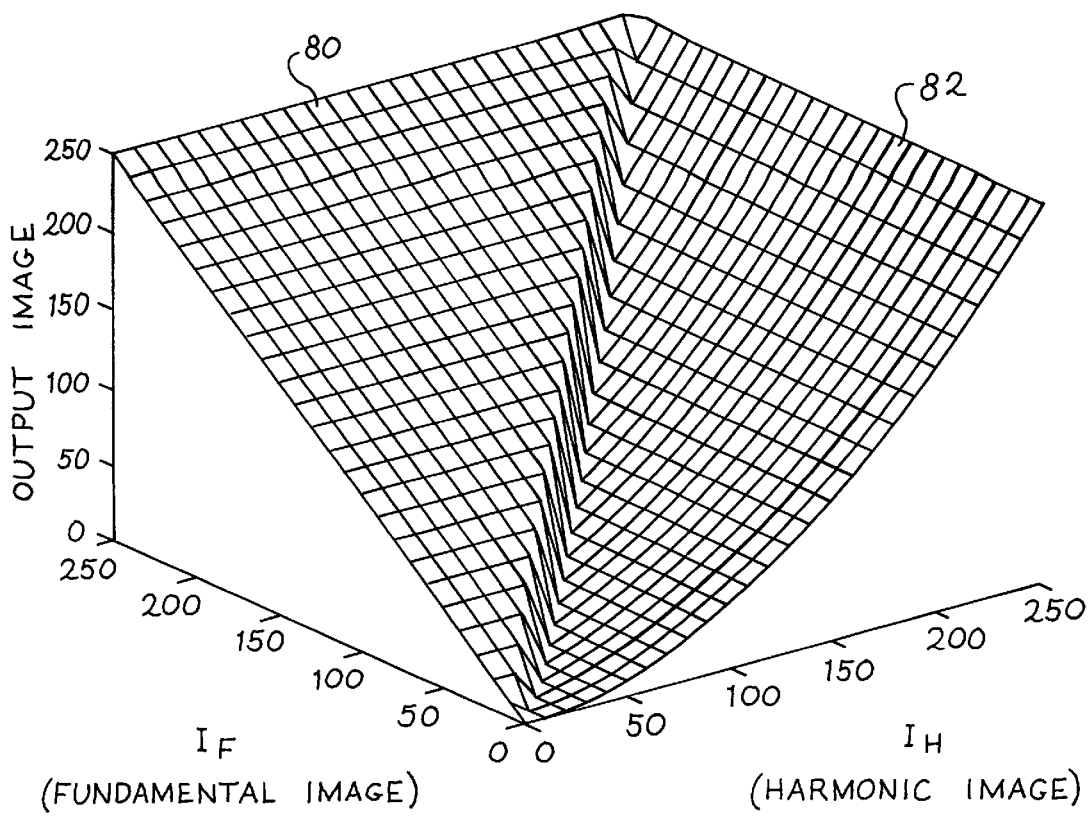
Fig. 8
Fig. 5
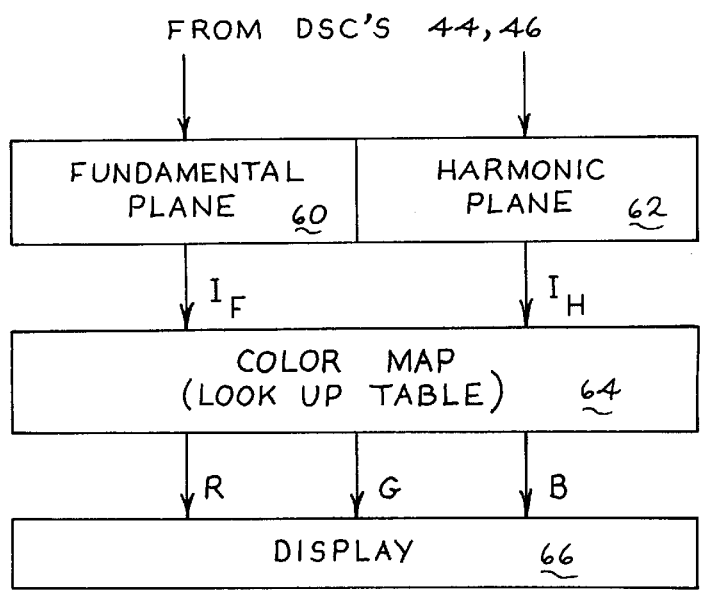

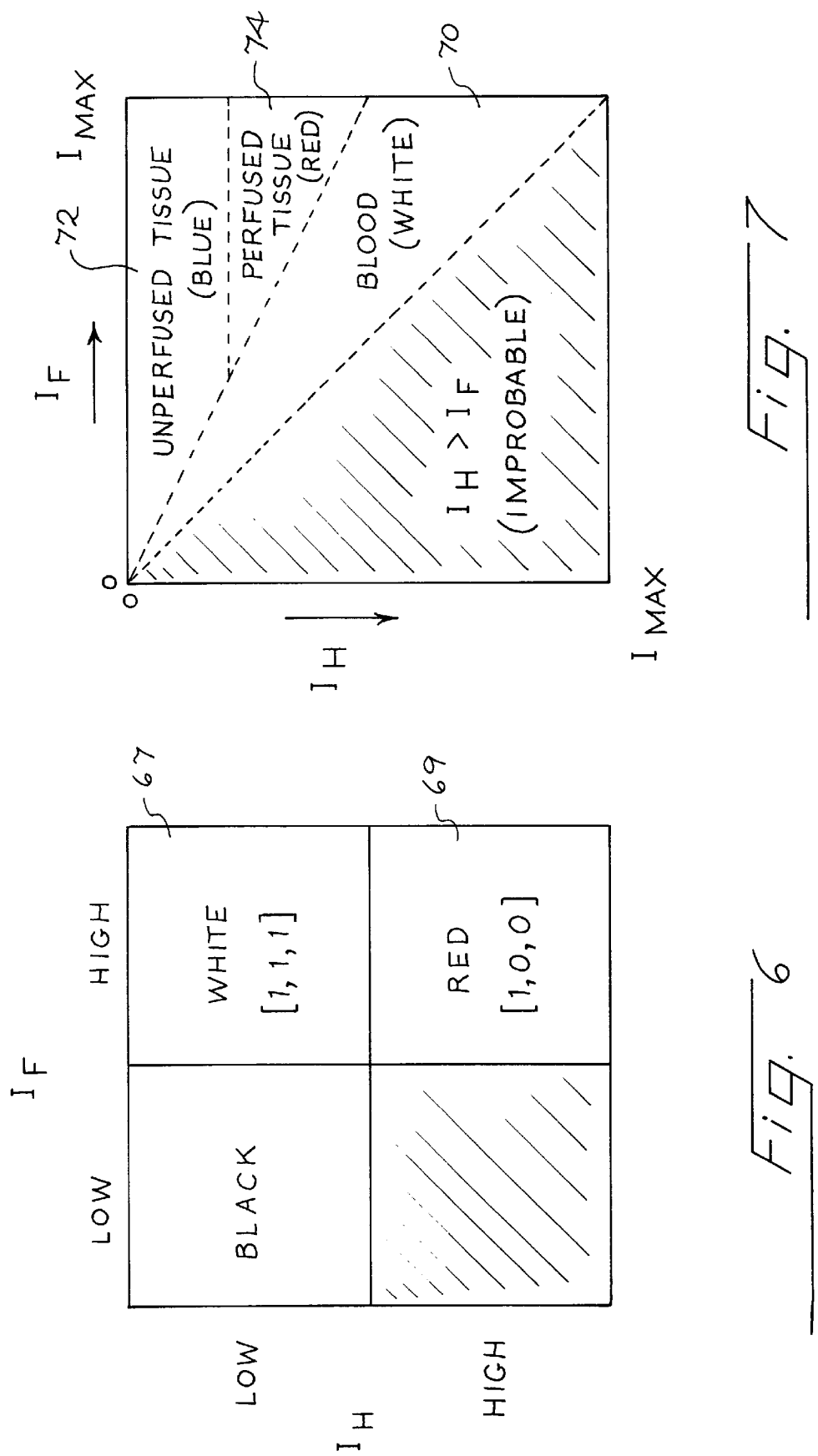

ULTRASOUND IMAGING ENHANCEMENT METHODS AND SYSTEMS

BACKGROUND OF THE INVENTION

This invention relates to ultrasound imaging systems, and in particular to methods and systems for simultaneously displaying image information derived from multiple imaging modes. This invention can be used to enhance the ultrasound image quality for moving or contrast agent-containing tissue structures, especially when imaging difficult-to-image patients where clutter or other stationary noise superimposed on the image makes high quality imaging of moving tissue structures difficult.

Conventional ultrasound image enhancement methods using only B-mode information may not work well in some cases where a good classification between the blood pool and moving tissue is difficult to achieve by using only the B-mode and/or processed B-mode information. Various image processing techniques have been developed to improve B-mode ultrasound images.

Lipshutz, U.S. Pat. No. 5,224,483, discloses a system for enhancing an ultrasound image by reducing clutter in a blood pool area of the image. The blood pool areas are identified using low-pass filtering and non-linear intensity mapping, and a mask image is then generated to have a first value in areas of tissue and substantially a second value in the areas of blood pool. The original image is then modulated with the mask image to substantially remove clutter in the blood pool.

Ustuner et al., U.S. Pat. No. 5,479,926, disclose another B-mode image enhancement method for combining a first image signal which has greater detail information and a second image signal which has greater contrast information, into a single image using a 2D look-up table. In one of the preferred embodiments, the second processed image can be obtained from a motion estimator which calculates the correlation coefficients between consecutive B-mode frames.

Arenson et al., U.S. Pat. No. 5,285,788, disclose a Doppler tissue imaging method (DTI) that uses color Doppler imaging means to image moving tissue so that stationary clutter can be removed or greatly suppressed since the Doppler signal is only sensitive to moving targets. The disclosed DTI imaging can output tissue velocity, energy, or acceleration as a two-dimensional image which is spatially coordinated and superimposed on a B-mode image to display simultaneously the selected Doppler information and a tomographic image of the moving tissue. For Doppler tissue velocity imaging (DTV), the moving tissue velocity is the primary parameter to be displayed. Conventionally, a color map is used to encode the direction as well as the magnitude of the velocities, and a gray scale B-mode image signal may also be partially added to provide tomographic information of the moving tissue, i.e., $$\bar{I}_o^{RGB} = \bar{C}^{RGB}(I_V) + \beta \cdot I_B,$$

where $\bar{I}_o^{RGB}$ is color coded output image, $\bar{C}^{RGB}$ represents the velocity color mapping function, $I_V$ represents Doppler tissue velocity, $I_B$ represents the gray scale B-mode image signal, and $\beta$ is a scaling factor with its value between 0 and 1.

Doppler tissue imaging provides a means to improve the moving tissue imaging with excellent stationary clutter noise suppression. In its video mix mode the Doppler signal from the moving tissue is mixed with the B-mode image, augmenting the B-mode image of moving tissue. However, the simple additive blending of the DTI image and the B-mode image does not fully utilize all the available information given by these two image signals.

In the past, various contrast agents have been used to enhance contrast of blood and perfused tissues. Typically, a contrast agent is introduced into a part of the body which is to be ultrasonically imaged. For example, in the case of a blood-filled chamber of the heart, blood which carries contrast agent can be distinctly imaged by detecting the contrast agent.

Nonlinear scattering from contrast agents is described, for example, by V. Uhlenhdorf, et al., in "Nonlinear Acoustic Response of Coated Microbubbles in Diagnostic Ultrasound" (1995 Ultrasonic Symposium, pp. 1559–1562). Such contrast agents possess a fundamental resonant frequency. When the contrast agents are insonified with a high intensity ultrasonic energy at this fundamental frequency, they reflect and radiate ultrasonic energy at both the fundamental frequency and a harmonic of the fundamental frequency. For example, if insonified at a frequency of 2.5 MHz, the contrast agent may radiate energy at both 2.5 MHz (the fundamental frequency) and at 5.0 MHz (the second harmonic frequency).

Typically, non-linear contrast agents are used with an imaging system having a transmit beamformer that transmits ultrasonic energy and a receive beamformer that receives the reflected ultrasonic energy. The transmit beamformer insonifies the area to be imaged with ultrasonic energy at a fundamental frequency. When insonified with ultrasonic energy at the fundamental frequency, the contrast agent radiates energy at both the fundamental and harmonic frequencies as described above. The receive beamformer receives both the fundamental and harmonic energy, filters out the fundamental energy, and forms a harmonic image from the received harmonic energy. Ideally, the harmonic image relates only to the scattering from the contrast agent.

The harmonic image, however, may contain harmonic frequency components related to scattering from tissues in addition to the desired harmonic energy. For example, the transmit beamformer may transmit energy at the harmonic frequency as well as at the fundamental frequency. This energy scatters linearly and is included in the harmonic image. In addition, the receive beamformer may not completely filter out energy at the fundamental frequency, so this fundamental frequency leaks into the harmonic image. Finally, non-linear scattering from tissues or non-linear propagation through tissues may result in harmonic energy being scattered from normal tissues and included in the harmonic image, even in the absence of a contrast agent.

Brock-Fisher et al., U.S. Pat. No. 5,577,505, combine a colorized non-linear image with a gray-scale image. The non-linear image is obtained via a subtraction approach, requiring insonifing the tissue at two different times and power levels. Further, the combination includes only the simple steps of colorizing the non-linear signal and summing with the gray-scale image.

Monaghan, U.S. Pat. No. 5,255,683, combines a B-mode image taken before the introduction of a contrast agent with a subtraction image formed from images taken after a contrast agent has been introduced. Monaghan, however, requires images to be acquired before and after the introduction of a contrast agent. The scan is thus not in real-time, and the scan plane must be identical for each firing before and after the introduction of the non-linear contrast agent.

SUMMARY OF THE INVENTION

The broadest aspects of the present invention are defined by the following independent claims. Generally, and without intending any limitation, a first aspect of the invention relates to the manner in which Doppler and B-mode image signals can be used to generate display indicia as a modulated, non-linear function of the Doppler and B-mode image signals. In this way portions of the B-mode image signal associated with moving tissue can be substantially enhanced and portions of the B-mode image signal associated with stationary tissue may be substantially suppressed, while avoiding saturation and flicker artifacts.

A second aspect of this invention relates to the manner in which an ultrasonic display image can be created as a function of fundamental and harmonic images. As described below, various approaches can be used for determining the output image as a function of the harmonic and fundamental images, and various techniques including color-coding can be used to distinguish the fundamental and harmonic components in the displayed image. The display of information related to the fundamental image provides the operator with information that allows the scan plane to be oriented easily and various components of the harmonic image to be identified easily.

The fundamental image may be optimized to provide good image quality independent of the harmonic image. Likewise, the harmonic image may be optimized for maximum fundamental rejection, with no consideration given to retaining the fundamental information component. Further, a combined image showing, for example, a ratio of the harmonic to the fundamental image intensities may contain more diagnostic information than either image alone.

BRIEF DESCRIPTION OF THE DRAWINGS

FIG. 1 is a block diagram of an ultrasonic imaging system suitable for use with this invention.

FIG. 5 is a block diagram of a portion of an ultrasonic imaging system.

FIG. 6 is a diagram representing a mapping function of another mode of operating the system of FIG. 1.

FIG. 7 is a diagram representing a mapping function of another mode of operating the system of FIG. 1.

FIGS. 8 and 9 are graphs of modulated, non-linear functions suitable for use in the look up table of FIG. 5.

DETAILED DESCRIPTION OF THE PRESENTLY PREFERRED EMBODIMENTS

Figure 2:
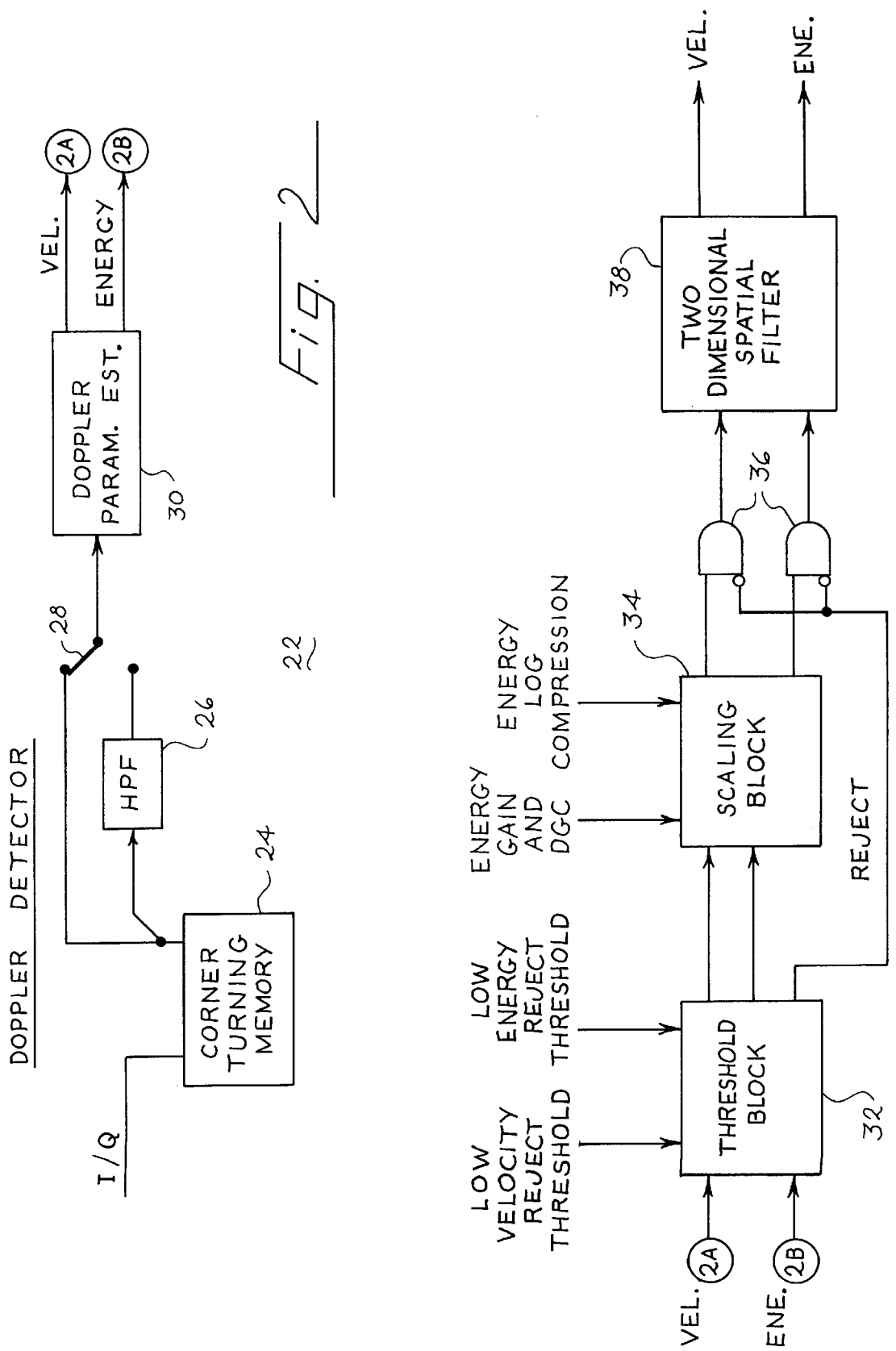
FIG. 2 is a block diagram of the Doppler detector of FIG. 1.

Alternative embodiments of this invention can take many forms. In the following discussion, a preferred imaging system architecture will first be described. Then the preferred embodiments will be described in two groups: the embodiments of the first group combine Doppler and B-mode images for display, while the embodiments of the second group combine fundamental and harmonic images for display.

PREFERRED IMAGING SYSTEM ARCHITECTURE

As pointed out below, a wide variety of ultrasonic imaging systems can be adapted for use with this invention. FIG. 1 shows one preferred architecture for a suitable ultrasound imaging system 10.

The imaging system 10 includes an ultrasonic transducer 12 which converts electrical ultrasonic frequency signals into sound energy, which is then emitted into a tissue T. Acoustic energy reflected from the tissue T is converted back to electrical signals by the transducer 12. A transmit beamformer 14 generates transmit waveforms that are applied to the transducer 12 to cause the transducer 12 to form transmit beams of ultrasonic energy, centered at a selected fundamental frequency.

Receive signals generated by the transducer 12 in response to reflected energy from the tissue T are formed into receive beams by a receive beamformer 16. The region from which reflected energy is formed into receive beams will be referred to as an imaged region, and may include blood, tissue, and optionally a non-linear contrast agent The receive beamformer 16 may be responsive to energy at the same frequency as that applied to the transducer by the transmit beamformer (the fundamental frequency) or at a different frequency which may be harmonically related to the transmit frequency (a harmonic frequency). The beamformed signals generated by the receive beamformer 16 are filtered by a programmable filter 18 which can be used to isolate desired signals from undesired signals. For example, the filter 18 may be programmed to reject signals at the fundamental frequency and to pass signals at a desired harmonic frequency, or vice-versa.

The filtered signals passed by the programmable filter 18 are preferably in the I/Q format, and they are applied to a B-mode detector 20 and a Doppler detector 22. The B-mode detector 20 converts receive signals from the filter 18 into detected and log compressed image signals. The Doppler detector 22 estimates the Doppler signal velocity and energy parameters. A preferred arrangement for the Doppler detector 22 is shown in FIG. 2.

Turning to FIG. 2, complex receive signals in the I/Q format are applied to a corner turning memory 24, which stores the samples until sufficient signals have been accumulated to allow Doppler measurements to be made. A high-pass filter 26 can optionally be used to provide greater rejection of signals from stationary and very slowly moving objects in the tissue. In Doppler tissue imaging the high-pass filter 26 is by-passed by a switch 28, and receive signals are passed directly from the corner turning memory 24 to a Doppler parameter estimator 30. The Doppler parameter estimator 30 estimates the mean velocity and the total energy of the Doppler signal, as is well known in the art.

The velocity and energy signals are then applied as inputs to a threshold block 32, which operates to reject signals from stationary and slowly moving objects. The threshold block 32 also receives inputs identifying a low velocity reject threshold and a low energy reject threshold. Signals from blood and noise can be removed by a low energy rejection threshold performed in the same block 32. In the threshold block, the measurement parameters are compared with application-specific threshold levels. If either of the signal parameters is below the respective threshold, then the entire acoustic sample is rejected, and the parameters are set to zero further down stream by the gates 36.

The scaling block 34 adds additional user-controlled gain to the log detected energy signal as well as additional user-controlled, depth-variable gain. In addition, the energy signal is log compressed to reduce the dynamic range of the signal and to make it suitable for display. The output signals generated by the gates 36 are applied to a two-dimensional spatial filter 38 that is used to smooth the Doppler signals and to remove noise and dropouts due to speckle and other variations.

Returning to FIG. 1, the B-mode, Doppler velocity, and Doppler energy signals generated by the detectors 20, 22 are applied as inputs to a memory 40, which stores multiple frames of acoustic data in preparation for scan conversion in order to allow convenient alignment of B-mode and Doppler images and to facilitate cine playback.

A processing block 42 is provided to select and perform additional processing on the Doppler velocity and energy parameters read from the memory 40. The block 42 operates to place any one of the following three parameters on the velocity/acceleration channel:

1. Velocity from a particular frame (N);
2. Average velocity determined from two frames (N and N-1);
3. Acceleration obtained from the difference between the velocity in a particular frame and the velocity of the previous frame (N and N-1).

The block 42 also places any of the following two parameters on the energy channel:

1. Energy from a particular frame (N); and
2. Average energy formed by averaging the energy of two frames (N and N-1).

A temporal filtering function may be selected (the second parameter in each of the above lists) to reduce noise and other variations. Such filtering may make the resulting images more aesthetically pleasing.

Digital scan converters 44, 46 are provided for the B-mode signal from the memory 40 and for the velocity/acceleration and energy signals from the processing block 42. The digital scan converters 44, 46 convert the respective signals from the acoustic grid to a raster grid suitable for display. If desired, the digital scan converters 44, 46 can be combined into a single scan converter if the reconstruction processing for the B-mode and Doppler information can be accomplished sequentially rather than in parallel. The B-mode detector 20 can be considered as forming a B-mode processor, and the Doppler detector 22 and the processing block 42 can be considered as a motion or Doppler processor.

The image signals supplied as outputs by the digital scan converters 44, 46 are stored in video image memories 48, 50. Each video image memory 48, 50 includes separate sections for storing frames of scan-converted image information for three separate parameters (B-mode image signals, velocity/acceleration image signals, and energy image signals). The two sets of memories 48, 50 are used in alternating fashion so that one set is used for display while the other is being updated. A multiplexer 52 is connected to the video image memories 48, 50, and the multiplexer 52 selects either the energy or the velocity/acceleration parameter for final color mapping.

A look-up table 54 is provided, which preferably comprises a random access memory arranged to form a two-dimensional look-up table. The B-mode image signal $I_B$ is used as an addressing input to the look-up table 54 and the Doppler image signal $I_D$ is used as a second addressing input to the look-up table 54. The look-up table 54 acts as a modulated, non-linear mapping system that maps the input signals $I_B$ and $I_D$ to output signals $I_o$. In this embodiment the output signal $I_o$ takes the form of three intensity values for red, green and blue parameters that are used to drive a video display 56. In alternate embodiments the output signal $I_o$ may be a scalar, monochromatic value. $I_B$, $I_D$ and $I_o$ are all two-dimensional arrays that are respective functions of x and y image coordinates.

The flexible 2D non-linear mapping performed by the look up table 54 can be used to construct the following output image signal $\overline{I}_o^{RGB}$:

$$\overline{I}_o^{RGB} = g(I_B) \, \overline{C}^{RGB}(I_D) + \beta \cdot I_B$$

where $g(I_B)$ is a function of $I_B$ and is given by $$g(I_B) = 0 \quad \text{if } I_B < b_1$$
$$= (I_B - b_1)/(b_2 - b_1) \quad \text{if } b_1 \leq I_B \leq b_2$$
$$= 1 \quad \text{if } I_B > b_2.$$

In this equation $\overline{C}^{RGB}$ represent the velocity color mapping function, $I_B$ represents the B-mode image signal, $I_D$ represents the Doppler image signal (Doppler velocity in this example), and $\beta$ is a scaling factor between 0 and 1. The velocity component of the output image signal $\overline{I}_o^{RGB}$ is modulated by $g(I_B)$. Of course, the description of an RGB mapping function is not intended to be limiting, and other color spaces such as the YUV space can be used if desired.

There are two advantages with this algorithm. First, by appropriately setting the values of $b_1$ and $b_2$, low intensity moving noise can be eliminated because the color output is effectively turned off when $I_B$ is very low ($I_B < b_1$). Second, the spatial resolution of the output image signal is determined by the high detail resolution B-mode image because the velocity output is modulated by the B-mode image. The effect of a narrow transition region $[b_1, b_2]$ is to create a natural, smooth transition between colored and uncolored regions.

The ultrasonic imaging system 10 described above is merely one example of a suitable system, and many variations are possible. Both analog and digital ultrasonic imaging systems can readily be adapted for use with this invention. For example, the Doppler detector 22 can take the form described in Arenson, U.S. Pat. No. 5,285,788. The ultrasonic imaging systems supplied by Acuson Corporation, the assignee of the present invention, under the tradenames Sequoia, Aspen, and 128XP can be adapted for use with this invention.

The receive beamformer of the Sequoia 512 system can be operated in a multiple-receive-beam mode, which increases the frame rate appreciably.

DOPPLER/B-MODE EMBODIMENTS

Figure 3:
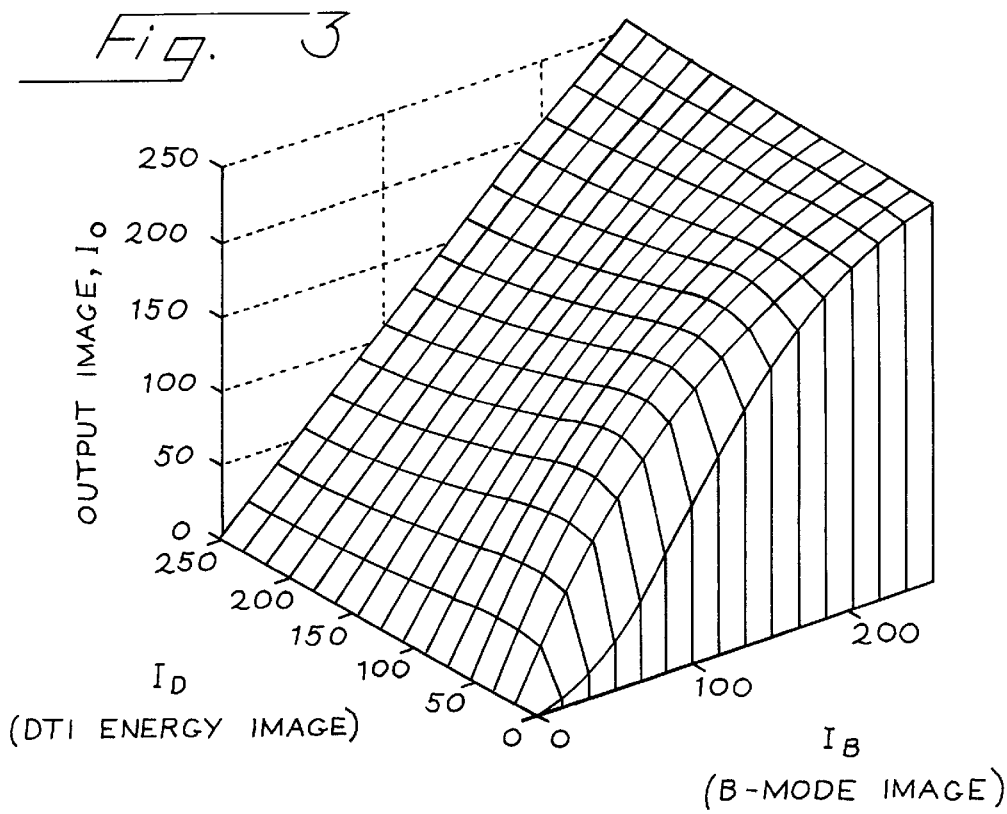
FIGS. 3 and 4 are graphs of modulated, non-linear functions suitable for use in the look-up table of FIG. 1.
Figure 4:
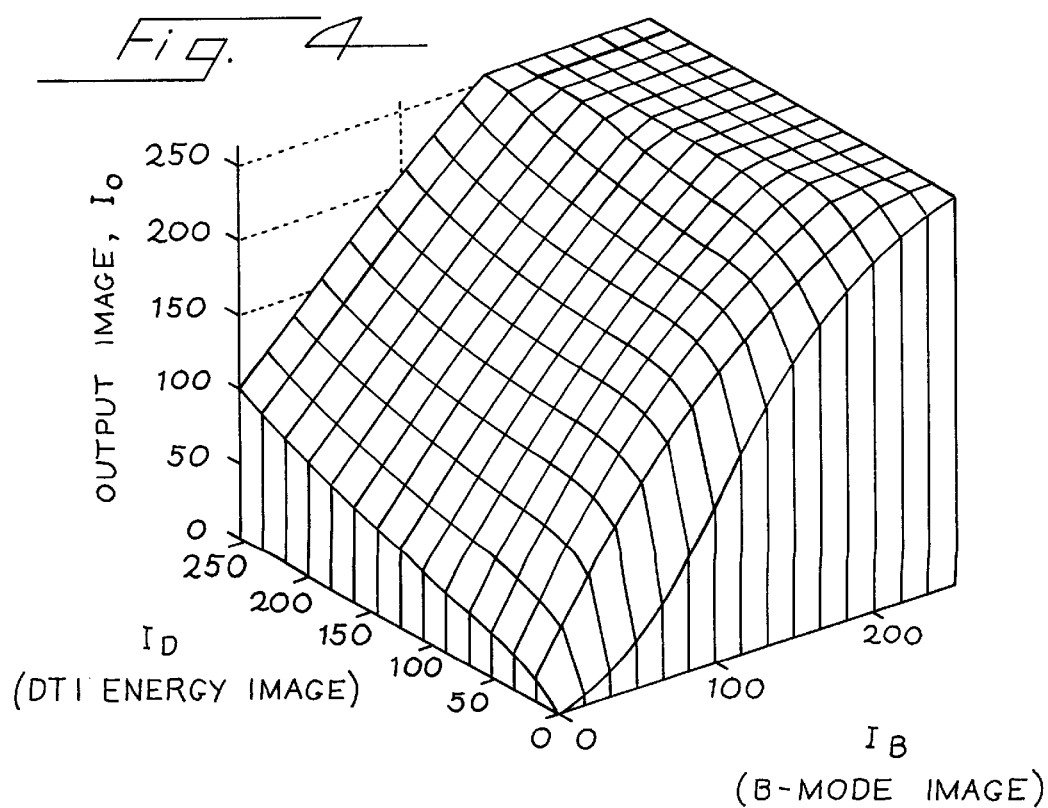

Turning now to FIGS. 3 and 4, these figures relate to embodiments of the present invention that display combinations of B-mode and Doppler images. The ultrasonic imaging system 10 of FIGS. 1 and 2 can be used, and in this case, the B-mode image signal $I_B$ is preferably a high-detail-resolution image signal, and the Doppler image signal $I_D$ preferably is optimized to discriminate among moving tissue, blood pool, and stationary clutter noise.

As shown in FIG. 1, the image signals $I_B$ and $I_D$ are applied as addressing inputs to the look-up table 54. In this preferred embodiment, the look-up table 54 takes the form of a two-dimensional table. Of course, a two dimensional table may be implemented as a conventional memory block addressed by two parameters or by a combination of two parameters. As described in greater detail below, the look-up table 54 stores display indicia as multi-bit intensity values. Selected ones of these stored intensity values, as indicated by the values of the addressing inputs $I_B$, $I_D$, are supplied as outputs to form the output image signal $I_o$ that is supplied to the display 26. Thus, the look-up table 54 functions as a generator for display indicia that in general are modulated as a non-linear function of the addressing input signals $I_B$ and $I_D$. Preferably, the mapping function implemented with the look-up table 54 greatly enhances the portion of the B-mode image $I_B$ corresponding to moving tissue (as indicated by the Doppler image signal $I_D$), and greatly suppresses portions of the B-mode image signal associated with stationary tissue (again as indicated by the Doppler image signal $I_D$).

The output image signal $I_o$ is generally a non-linear, two-dimensional function of $I_B$ and $I_D$:

$$I_o = F(I_B, I_D)$$

Because the look-up table 54 provides modulated, non-linear mapping, the information provided by the image signals $I_B$ and $I_D$ can be used optimally. Since $I_D$ is not directly displayed or mixed with $I_B$, but is instead used as an addressing input to the look-up table 54, a suitably selected set of values for the look-up table can be used to enhance moving tissues and suppress stationary tissues that appear in the B-mode image $I_B$. In this way, the ratio between the output signal $I_o$ associated with moving tissue and the output signal $I_o$ associated with clutter noise can be greatly increased, while preserving the excellent detail resolution provided by the B-mode image $I_B$.

Furthermore, a Doppler processor such as the detector 22 calculates the velocity of the moving target from Doppler pulse samples at a high sampling rate, which is often about a few kilohertz. This provides sufficient frequency bandwidth to discriminate different moving targets of various velocities, and is well suited for use with fast moving tissue parts such as mitral valves for cardiology applications.

The function $F(I_B, I_D)$ can take many forms. For example, the output image signal $I_o$ can be a colored image with the amount of color (color saturation) proportional to the amount of enhancement provided to moving tissue. In this case, the function $F(I_B, I_D)$ is essentially a two-variable, non-linear, vector function, with red, green, and blue components. When the three components are set to be equal to one another, $I_o$ becomes a gray-scale image.

It should be noted that the display indicia generator may take other forms than a look-up table. Arbitrary, non-linear, two-dimensional functions can also be implemented with hardware or cascaded hardware that implements a series of piecewise linear functions to approximate the desired 2D non-linear function.

FIG. 3 shows one preferred embodiment of the function $F(I_B, I_D)$ stored in the 2D look-up table 54 of FIG. 1. The embodiment of FIG. 3 provides an enhanced gray-scale image for the output signal $I_o$. In this embodiment, $I_D$ preferably corresponds to a Doppler tissue image (energy mode) as disclosed in Arenson, U.S. Pat. No. 5,285,788. As shown in FIG. 3, the function $F(I_B, I_D)$ is a non-linear, two-dimensional function of $I_D$ and $I_B$. If $I_D$ is zero or very small (which corresponds to blood pool or stationary components of the image), the mapping function from $I_B$ to $I_o$ strongly suppresses the low-to-medium levels of $I_B$. In this way, blood pool is made darker and clutter noise is reduced. When the Doppler image signal $I_D$ is in a low-to-medium level range (associated with weak-to-moderate signals for moving tissue and often corresponding to a moving wall boundary), the mapping from $I_B$ to $I_o$ strongly enhances low level values of $I_B$. The amount of enhancement is gradually reduced as $I_B$ increases. In this way, moving wall boundaries that are typically hard to see are enhanced. For large values of $I_D$ (corresponding to strong signals from moving targets), the mapping of $I_B$ to $I_o$ gradually approaches a linear mapping. The function shown in FIG. 3 sufficiently enhances the signals from moving tissue at low values of $I_D$ without saturating the high intensity signals associated with stationary or moving tissue. In addition, the function shown in FIG. 3 has a smooth transition when $I_D$ goes from zero to greater than zero, thereby avoiding flashing artifacts seen in certain prior-art methods.

Table 1 provides a listing of numerical values that can be used for the look-up table of FIG. 3. In this case, the output $I_o$ is an 8 bit number ranging between 0–255. In Table 1, only sub-sample data are shown. The full look-up table is implemented using two-dimensional linear interpolation between the listed values of Table 1.

TABLE I

| | | | | | | | | $I_B \rightarrow$ | | | | | | | | |
|---|---|---|---|---|---|---|---|---|---|---|---|---|---|---|---|---|
| | 0 | 4 | 14 | 30 | 52 | 76 | 102 | 129 | 154 | 177 | 198 | 215 | 229 | 240 | 249 | 255 |
| | 0 | 32 | 62 | 88 | 111 | 132 | 151 | 168 | 184 | 197 | 210 | 221 | 231 | 240 | 248 | 255 |
| | 0 | 35 | 65 | 93 | 117 | 138 | 157 | 174 | 189 | 202 | 214 | 224 | 233 | 241 | 249 | 255 |
| | 0 | 34 | 64 | 90 | 114 | 136 | 154 | 171 | 186 | 200 | 212 | 223 | 232 | 241 | 248 | 255 |
| | 0 | 32 | 60 | 86 | 109 | 130 | 149 | 166 | 182 | 196 | 208 | 220 | 230 | 239 | 247 | 255 |
| | 0 | 30 | 57 | 81 | 104 | 125 | 144 | 161 | 177 | 191 | 204 | 216 | 227 | 237 | 247 | 255 |
| | 0 | 28 | 53 | 77 | 99 | 119 | 138 | 155 | 171 | 186 | 200 | 213 | 225 | 235 | 246 | 255 |
| $I_D$ | 0 | 26 | 50 | 73 | 94 | 114 | 132 | 150 | 166 | 182 | 196 | 209 | 222 | 234 | 245 | 255 |
| $\downarrow$ | 0 | 24 | 47 | 69 | 90 | 109 | 128 | 145 | 162 | 177 | 192 | 206 | 219 | 232 | 244 | 255 |
| | 0 | 23 | 45 | 66 | 86 | 105 | 124 | 141 | 158 | 174 | 189 | 203 | 217 | 230 | 243 | 255 |
| | 0 | 22 | 43 | 63 | 83 | 102 | 120 | 137 | 154 | 170 | 186 | 201 | 215 | 229 | 242 | 255 |
| | 0 | 21 | 42 | 61 | 80 | 99 | 117 | 134 | 151 | 167 | 183 | 199 | 213 | 228 | 242 | 255 |
| | 0 | 20 | 40 | 59 | 78 | 97 | 114 | 132 | 149 | 165 | 181 | 197 | 212 | 227 | 241 | 255 |
| | 0 | 20 | 39 | 58 | 77 | 95 | 112 | 130 | 147 | 163 | 179 | 195 | 211 | 226 | 241 | 255 |
| | 0 | 19 | 38 | 57 | 75 | 93 | 110 | 128 | 144 | 161 | 177 | 194 | 209 | 225 | 240 | 255 |

FIG. 4 shows another two-dimensional, non-linear mapping function which is a variation of that shown in FIG. 3, and which is also suitable for use in the look-up table 54. The main difference between the functions mapped in FIGS. 3 and 4 is that in FIG. 4 the initial offset of the mapping from $I_B$ to $I_o$ slightly increases with increasing values of $I_D$. The effect of this increase is to increase the overall (global) image contrast slightly, since the Doppler image signal also contributes partially to global contrast of the output image $I_o$. Clipping or saturation of the output signal $I_o$ when both $I_D$ and $I_B$ are at very high levels is not of critical concern, as relatively few image pixels simultaneously have very high levels for both $I_D$ and $I_B$ in clinical imaging conditions. Table 2 provides a listing of the values plotted in FIG. 4, in the same format as Table 1 discussed above.

TABLE 2

| $I_B \rightarrow$ | | | | | | | | | | | | | | | | |
|---|---|---|---|---|---|---|---|---|---|---|---|---|---|---|---|---|
| | 0 | 4 | 14 | 30 | 52 | 76 | 102 | 129 | 154 | 177 | 198 | 215 | 229 | 240 | 249 | 255 |
| | 15 | 45 | 72 | 96 | 119 | 140 | 159 | 176 | 192 | 206 | 219 | 231 | 242 | 252 | 255 | 255 |
| | 22 | 54 | 82 | 108 | 131 | 152 | 171 | 188 | 203 | 217 | 230 | 242 | 252 | 255 | 255 | 255 |
| | 28 | 59 | 87 | 112 | 135 | 156 | 174 | 192 | 207 | 222 | 234 | 246 | 255 | 255 | 255 | 255 |
| | 34 | 63 | 89 | 114 | 136 | 157 | 175 | 193 | 209 | 223 | 237 | 249 | 255 | 255 | 255 | 255 |
| | 39 | 66 | 92 | 115 | 137 | 157 | 176 | 193 | 209 | 224 | 238 | 251 | 255 | 255 | 255 | 255 |
| | 44 | 70 | 94 | 117 | 138 | 158 | 176 | 194 | 210 | 225 | 240 | 253 | 255 | 255 | 255 | 255 |
| $I_D$ | 50 | 74 | 97 | 119 | 139 | 159 | 177 | 195 | 211 | 227 | 242 | 254 | 255 | 255 | 255 | 255 |
| $\downarrow$ | 56 | 79 | 101 | 122 | 142 | 161 | 179 | 196 | 213 | 229 | 244 | 255 | 255 | 255 | 255 | 255 |
| | 62 | 84 | 105 | 125 | 145 | 163 | 182 | 199 | 216 | 232 | 247 | 255 | 255 | 255 | 255 | 255 |
| | 68 | 89 | 110 | 129 | 149 | 167 | 185 | 202 | 219 | 236 | 251 | 255 | 255 | 255 | 255 | 255 |
| | 75 | 95 | 115 | 134 | 153 | 172 | 189 | 207 | 224 | 240 | 255 | 255 | 255 | 255 | 255 | 255 |
| | 82 | 102 | 121 | 140 | 159 | 177 | 195 | 212 | 229 | 245 | 255 | 255 | 255 | 255 | 255 | 255 |
| | 90 | 109 | 128 | 147 | 165 | 183 | 201 | 218 | 235 | 252 | 255 | 255 | 255 | 255 | 255 | 255 |
| | 100 | 119 | 137 | 156 | 174 | 191 | 209 | 226 | 243 | 255 | 255 | 255 | 255 | 255 | 255 | 255 |

The present invention can be adapted for use with many types of Doppler and B-mode images. For example, either or both of the B-mode image $I_B$ and the Doppler image $I_D$ may be a harmonic image, such as a second harmonic image. For example, the B-mode image $I_B$ may be a second harmonic B-mode image with good detail resolution and reduced clutter, while the Doppler image $I_D$ may be a conventional Doppler tissue energy image of the type described in Arenson U.S. Pat. No. 5,285,788. This combination of images provides important advantages. Because the B-mode image is a second harmonic image, it has excellent detail resolution (both lateral and temporal). Because the Doppler tissue energy image is used to discriminate moving from stationary tissue, this image may be a relatively low resolution image with a large acoustic line spacing to enhance the frame rate. The output image $I_o$ thus combines the high detail resolution of the B-mode image with the motion discrimination of the Doppler image. Other Doppler tissue images (such as images based on velocity or acceleration) may be substituted for the Doppler tissue energy images discussed above. These particular combinations of images are particularly useful in cardiac imaging applications.

As used herein, a Doppler tissue image is a Doppler image in which substantially no clutter filtering is performed such that Doppler parameters (such as energy, velocity, acceleration, and combinations thereof) are available for tissue having a Doppler velocity as low as about 1 mm/sec.

Furthermore, it has been surprisingly discovered that contrast agent is not required in all embodiments to provide improved B-mode images when one of the image signals $I_B$, $I_D$ is a non-linear image such a second harmonic image.

Though a Doppler tissue energy image is preferred for the Doppler image $I_D$, other Doppler images can be used, such as Doppler tissue velocity images, Doppler tissue acceleration images, Doppler flow velocity images, Doppler flow energy images, and so forth. In an alternate embodiment, for example, the Doppler image $I_D$ can be obtained using Doppler flow velocity signals. The intensity of the B-mode image can be selectively reduced in regions having high flow velocity, thus suppressing clutter and blood pool and enhancing the border definition in the B-mode image. In general, the widest variety of combinations of B-mode image and Doppler information image can be used to enhance the display of the B-mode signal.

The embodiments described above provide important advantages. Image regions associated with moving tissue can be selectively enhanced, and visualization can consequently be improved in an image which provides both high sensitivity to motion and high detail resolution. Stationary clutter noise can be removed or greatly suppressed in the output image $I_o$ to improve the ratio between the intensities of portions of the displayed image associated with moving tissue and portions of the displayed image associated with clutter noise. This provides important advantages in the detection of endocardium border for difficult-to-image patients where stationary clutter noise is strong and may tend to obscure the moving border.

The use of a look-up table to implement the two-dimensional non-linear function F ($I_B$, $I_D$) offers maximal flexibility. Any desired non-linear function can be loaded to enhance the use of Doppler information provided by the addressing input $I_D$ so as to achieve the desired enhancement of the moving tissue image of the original B-mode image while removing or strongly suppressing stationary clutter noise. When color enhancement of the output signal $I_o$ is a function of tissue movement, the visualization of moving tissue structures is further enhanced.

The non-linear mapping functions described above provide particular advantages over the prior-art approaches of additive mixing, gating or even a combination of additive mixing and gating. Additive mixing does not suppress stationary clutter, because stationary clutter in the B-mode signal $I_B$ is simply displayed. Furthermore, when the amount of enhancement for moving tissue is proportional to $I_D$, additive mixing may overenhance regions having a strong signal $I_D$ as well as a strong signal $I_B$, thereby causing saturation, and may also underenhance weak signals for moving tissue which are often difficult to see in the original B-mode image.

Prior-art gating approaches can assist in removing stationary clutter. However, because moving tissue generally stops moving momentarily during the transition from one heartbeat to the next, a gated output signal will rapidly flash its value between $I_B$ and 0 and back again, thereby creating a strong flashing artifact. In addition, the moving tissue signal is not used to enhance the B-mode signal. A combination of additive mixing and gating is still plagued by the overenhancement problems and the flashing artifact problems described above.

FUNDAMENTAL/HARMONIC EMBODIMENTS

FIGS. 5–9 relate to another class of embodiments of the present invention, which combine fundamental and harmonic images for display.

The imaging system 10 of FIG. 1 may be used, and in this case the tissue being imaged preferably includes a nonlinear contrast agent such as that described above. Any suitable contrast agent may be used, as long as it absorbs ultrasonic energy at a first frequency and reflects ultrasonic energy at a second frequency, different from the first frequency. In this example, the first frequency is referred to as the fundamental frequency, and the second frequency is a harmonic of the first frequency. As used herein, "harmonic" is intended broadly to include sub-harmonics and fractional harmonic energy (e.g. ½ or ³⁄₂ of the fundamental), as well as higher harmonics (e.g. 2 or 3 times the fundamental).

When the imaging system 10 of FIG. 1 is used to collect both fundamental and harmonic image signals, the programmable filter 18 is preferably programmed to remove either the fundamental frequency components or the harmonic frequency components from selected acoustic lines or frames to generate the desired signal, which may then be passed either to the B-mode detector 20 or the Doppler detector 22. It should be understood that the fundamental and harmonic images may be generated in a number of different ways.

In one mode of operation, both the fundamental and harmonic images are generated from signals detected by the B-mode detector 20. In a preferred mode of operation, either or both of the fundamental and harmonic images are generated from signals detected by the Doppler detector 22 with no clutter filtering. In alternate modes of operation, the Doppler detector 22 (which functions as a motion processor) is operated in a color Doppler mode such as velocity, energy, tissue velocity, or tissue energy mode to produce the harmonic image signal.

For example, in one mode of operation either the fundamental or the harmonic image is generated by the Doppler detector 22 operating in an energy mode with no clutter filtering and with the conventional low-velocity rejection threshold disabled. The Doppler detector 22 therefore emulates a form of B-mode processing. In this mode, one image (fundamental or harmonic) is generated by the B-mode detector 20 and the other image is generated by the Doppler detector 22. The images are then combined by the mapping process described below. Fundamental and harmonic frequency images may be generated simultaneously or from separate line firings. When using separate line firings, fundamental and harmonic firings can alternate on a line-by-line, line-group by line-group, or frame-by-frame basis. The harmonic image may also be generated over only a portion of the scan region to preserve the frame rate. The B-mode detector 20 may also be used to sequentially process both the fundamental and harmonic frequency images. Preferably, the receive beamformer 16 operates in a multiple simultaneous receive beam mode such that multiple fundamental and/or harmonic receive beams may be generated from a single transmit firing, thereby increasing the frame update rate on the display 56.

FIG. 5 shows a preferred embodiment of the invention utilizing the ultrasound system of FIG. 1. The ultrasound system generates fundamental and harmonic images in raster display format for storage in separate image plane memories 60, 62 (which may correspond to separate sections of the memory 50 of FIG. 1). The fundamental and harmonic image plane memories 60, 62 are coupled to a look-up table 64 that generates RBG values for a display device 66. Given any two input signals, $I_F$, $I_H$, the look-up table 64 generates display indicia representative of any desired functional combination of the two input signals. For example, the scan converters 44, 46 calculate for each point (x,y) in the scanned image a fundamental intensity value $I_F(x,y)$ and a harmonic intensity value $I_H(x,y)$ which may be stored in the respective image plane memories 60, 62. The fundamental and harmonic intensity values $I_F(x,y)$, $I_H(x,y)$ stored in the image plane memories 60, 62 are provided as inputs to a mapping function $f(I_F(x,y), I_H(x,y))$ implemented by the look-up table 64. A similar mapping function implemented with a look-up table for use with various signals including high contrast and low contrast signals is disclosed in U.S. Pat. No. 5,479,926 to Ustuner et al. "Imaging System Display Processor," which is incorporated by reference.

The look-up table 64 generates display indicia P(x,y) based on the harmonic and fundamental frequency information stored in the image plane memories 60, 62 and outputs the display indicia to the display device 66. Algebraically, the mapping operation may be represented by the function:

$$P(x,y)=f(I_F(x,y), I_H(x,y)).$$

The display indicia P(x,y) may represent either a gray-scale value or color values R, G, and B.

The preferred embodiment described above can provide simultaneous display of fundamental and harmonic images in several modes of operation using different mapping functions provided by the look-up table 64. For example, the display indicia may be a gray-scale or color display value. FIG. 6 shows a first mapping function that uses fundamental frequency information $I_F(x,y)$ to determine the display indicia intensity or brightness, and the harmonic information $I_H(x,y)$ to determine the display indicia hue or color. The hue or color may be conventionally represented as a [R,B,G] value. For example, at $I_H(x,y)=0$, a color mapping function C may use the color white ([1,1,1]) as the display indicia, and at $I_H(x,y)=I_H$Max (some maximum value) the color function C may use the color red ([1,0,0]) as the display indicia. Normal tissue can thus be displayed as white at region 67 and blood/contrast agent can be displayed as red at region 69. The mapping function can be described as:

$$P(x,y)=I_F(x,y)^* \; C(I_H(x,y)).$$

FIG. 8 is a graphical representation of a mapping function that provides a gray-scale output signal in a region 80 (in which the fundamental value $I_F(x,y)$ is greater than the harmonic value $I_H(x,y)$), and a color output signal in a region 82 (in which the fundamental value $I_F(x,y)$ is less than the harmonic value $I_H(x,y)$).

Figure 9:
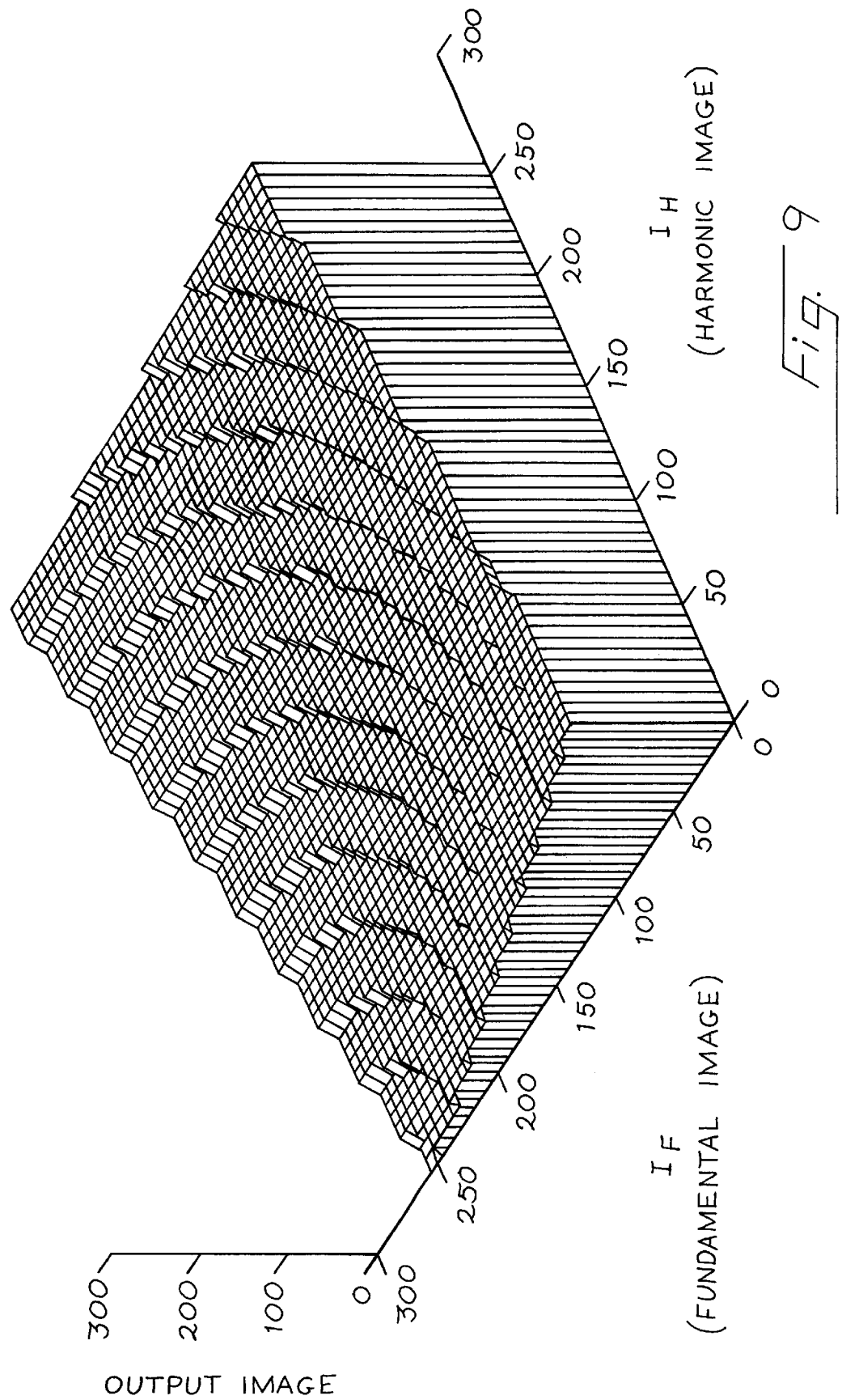

FIG. 9 is a graphical representation of another mapping function that suppresses the value of the output signal P(x,y) in region characterized by a high fundamental value $I_F(x,y)$ and a low harmonic value $I_H(x,y)$. In this way, high intensity portions of the harmonic image $I_H(x,y)$ that are associated with feedthrough or leakage of ultrasonic energy that is linearly scattered from tissue are deemphasized in the output image.

Alternatively, the display intensity can be determined by a function such as the maximum of the fundamental or the harmonic frequency intensity, $\max(I_F(x,y), I_H(x,y))$, which can be represented by the function:

$$P(x,y)=\max(I_F(x,y),I_H(x,y))^* \; C(I_H(x,y)).$$

In another mode of operation, the display indicia, such as color, can be determined by the ratio of harmonic frequency intensity to fundamental frequency intensity, $I_H(x,y)/I_F(x,y)$. For example, the fundamental intensity is ordinarily greater than the harmonic intensity ($I_F(x,y)>I_H(x,y)$) because in ordinary tissue the density of non-linear contrast agent is low. When the harmonic frequency intensity is greater than the fundamental frequency intensity ($I_F(x,y)<I_H(x,y)$), the region typically contains a greater amount of non-linear contrast agent, indicating a perfused region. Thus, the ratio of signal intensity at harmonic and fundamental frequencies may provide information about the relative density of non-linear scatterers. The mapping function can then be configured to cause a transition of display indicia at the transition from a non-perfused to a perfused region.

As shown in FIG. 7, three or more colors may be used to distinguish blood (region 70), unperfused tissue (region 72), and perfused tissue (region 74). The color mapping function, $C_t$, may return a color value from blue-green (unperfused) to red (perfused) as a function of the harmonic frequency intensity. The transition to red occurs at levels of harmonic frequency intensity associated with perfused tissue. The mapping function $\alpha(I_H(x,y)/I_F(x,y))$ ranges from a value of 0 when $I_H$ is equal to zero and to a value of 1 when $I_H$ is greater than or equal to $I_F$. The color $C_b$ (which may be yellow for example) is used to display blood. The hue or color is then determined by the function:

$$C(x,y) = (1-\alpha(I_H(x,y)/I_F(x,y))) * C_t(I_H(x,y)) + \alpha(I_H(x,y)/I_F(x,y)) * C_b,$$

and intensity by the maximum of $I_H(x,y)$ and $I_F(x,y)$:

$$P(x,y) = \max(I_H(x,y)/I_F(x,y)) * C(I_H(x,y)/I_F(x,y)).$$

In another mode of operation, the ratio of the harmonic to the fundamental image intensity can be displayed directly as an image, using either gray-scale or color-coded intensities. Also, fundamental and harmonic images can be separately encoded as color images with two different color schemes (such as a gray-scale for the fundamental, and a red-orange scale for the harmonic). At each point in the display, one of the two images is selected via pixel controlled threshold logic. For example, at each pixel the pixel representing higher energy can be selected for display.

In yet another mapping function, more than two image planes may be combined. For example, an image may combine an unfiltered harmonic energy image (the harmonic B-mode signal), a filtered harmonic energy or velocity image (harmonic CDV or CDE) and a fundamental B-mode image to form a single color display image. Multiple, cascaded look up tables or a single look up table having more than two dimensions can be used.

Simultaneously displaying the harmonic image with the fundamental image allows easier orientation of the scan plane and identification of harmonic flows. In the foregoing embodiments, fundamental image quality may be optimized independently of the harmonic image so that the fundamental image information may be used for diagnostic purposes as well as orientation. Likewise, the harmonic information may also be optimized for maximum fundamental rejection without interfering with the fundamental components.

CONCLUSION

The foregoing description is intended to illustrate a few of the many forms that the present invention may take, and many alternatives are possible. For example, the image signals may be obtained at various points upstream of the scan converters, and the non-linear mapping may be performed before scan conversion. When more than two image signals are combined, some may be mapped prior to scan conversion and others after scan conversion. It is only the following claims, including all equivalents, that are intended to define the scope of the invention.

We claim:

1. A method for ultrasonically imaging comprising the following steps:

(a) generating a Doppler image signal representative of an imaged region;

(b) generating a B-mode image signal representative of the imaged region; and (c) generating individual display indicia representative of the imaged region as a modulated, non-linear function of both the Doppler and B-mode image signals.

2. The method of claim 1 wherein at least one of steps (a) and (b) generates the respective image signal using a harmonic frequency of an associated transmit center frequency.

3. The method of claim 2 wherein steps (a) and (b) are performed without added contrast agent in the imaged region.

4. The method of claim 1 wherein step (c) comprises the step of applying the image signals as inputs to a multi-bit look-up table.

5. The method of claim 4 wherein the look-up table comprises two dimensions of data addressing.

6. The method of claim 1 wherein the imaged region comprises moving tissue and stationary tissue, and wherein step (c) comprises the step of selecting the non-linear function to substantially enhance portions of the B-mode image signal associated with moving tissue and to substantially suppress portions of the B-mode image signal associated with stationary tissue.

7. The method of claim 1 wherein the Doppler image signal comprises a Doppler tissue image signal.

8. The method of claim 1 wherein the Doppler image signal comprises a Doppler flow image signal.

9. The method of claim 1, 7 or 8 wherein step (a) comprises the step of generating the Doppler image signal as a function of Doppler velocity.

10. The method of claim 1, 7 or 8 wherein step (a) comprises the step of generating the Doppler image signal as a function of Doppler energy.

11. The method of claim 1, 7 or 8 wherein step (a) comprises the step of generating the Doppler image signal as a function of Doppler acceleration.

12. The method of claim 1 wherein the tissue comprises cardiac tissue.

13. The invention of claim 1 wherein the step (a) comprises the step of generating the Doppler image signal with a first acoustic line spacing, wherein step (b) comprises the step of generating the B-mode image signal with a second acoustic line spacing, wherein the first acoustic line spacing is greater than the second acoustic line spacing, and wherein step (c) comprises the step of generating the display indicia representative of the imaged region and associated with a plurality of acoustic lines.

14. The invention of claim 1 wherein step (c) comprises the step of generating the display indicia representative of a two-dimensional representation of the imaged region.

15. An ultrasonic imaging system comprising:

a first processor operative to generate a Doppler image signal representative of an imaged region;

a second processor operative to generate a B-mode image signal representative of the imaged region; and a generator responsive to the first and second processors, said generator generating individual display indicia representative of the imaged region as a modulated, non-linear function of both the Doppler image signal and the B-mode image signal.

16. The invention of claim 15 wherein at least one of the first and second processors is responsive to a harmonic frequency of an associated transmit center frequency.

17. The invention of claim 15 wherein the generator comprises a multi-bit look-up table.

18. The invention of claim 17 wherein the look-up table comprises two dimensions of data addressing.

19. The invention of claim 18 wherein the look up table comprises more than two dimensions of data addressing.

20. The invention of claim 15 wherein the imaged region comprises moving tissue and stationary tissue, and wherein the non-linear function of the generator is selected to substantially enhance portions of the B-mode image signal associated with moving tissue and to substantially suppress portions of the B-mode image signal associated with stationary tissue.

21. The method of claim 15 wherein the Doppler image signal comprises a Doppler tissue image signal.

22. The method of claim 15 wherein the Doppler image signal comprises a Doppler flow image signal.

23. The method of claim 15, 21 or 22 wherein the first processor is structurally adapted to generate the Doppler image signal as a function of Doppler velocity.

24. The method of claim 15, 21 or 22 wherein the first processor is structurally adapted to generate the Doppler image signal as a function of Doppler energy.

25. The method of claim 15, 21 or 22 wherein the first processor is structurally adapted to generate the Doppler image signal as a function of Doppler acceleration.

26. The method of claim 15 wherein the imaged region comprises cardiac tissue.

27. The invention of claim 15 wherein the Doppler and B-mode image signals are characterized by respective acoustic line spacings, wherein the Doppler image signal acoustic line spacing is greater than the B-mode image signal acoustic line spacing, and wherein the generator generates the display indicia for a region associated with a plurality of acoustic lines included in the imaged region.

28. In a method for ultrasonically imaging a target comprising the step of transmitting ultrasonic energy into a tissue at a fundamental frequency, the improvement comprising:
   (a) generating a fundamental frequency intensity value in response to reflections from the tissue;
   (b) generating a harmonic frequency intensity value in response to reflections from the tissue; and
   (c) generating individual display indicia as a function of both the fundamental and harmonic frequency intensity values.

29. The method of claim 28 wherein the display indicia include brightness levels.

30. The method of claim 28 wherein the display indicia include gray scale levels.

31. The method of claim 28 wherein the gray scale levels are a function of the fundamental frequency intensity value.

32. The method of claim 28 wherein the display indicia include colors.

33. The method of claim 32 wherein the colors are a function of the fundamental frequency intensity value.

34. The method of claim 28 wherein the display indicia comprise brightness levels which are a function of the maximum of the fundamental frequency and harmonic frequency intensity values.

35. The method of claim 28 wherein the display indicia comprise colors which are a function of the ratio of the harmonic intensity value to the fundamental intensity value.

36. The method of claim 28 wherein step (a) comprises the step of using a Doppler processor to generate the fundamental frequency intensity value.

37. The method of claim 28 wherein step (b) comprises the step of using a Doppler processor to generate the harmonic frequency intensity value.

38. The method of claim 28 wherein step (c) comprises the step of applying the fundamental and harmonic frequency intensity values to a look-up table.

39. The method of claim 28 wherein step (c) comprises the step of using a mapping function operative to de-emphasize regions of an image having a high fundamental frequency intensity value and a low harmonic frequency intensity value.

40. The method of claim 28 wherein step (c) comprises the step of using a modulated non-linear mapping function to map the fundamental and harmonic intensity values to display indicia.

41. The method of claim 28 further comprising the step of:
   (d) interleaving steps (a) and (b) on a line-by-line basis, wherein the display indicia generated in step (c) are representative of at least a portion of the imaged region associated with a plurality of lines.

42. The method of claim 28 further comprising the step of:
   (d) interleaving steps (a) and (b) on a plurality-of-lines by plurality-of-lines basis, wherein the display indicia generated in step (c) are representative of at least a portion of the imaged region associated with a plurality of lines.

43. The method of claim 28 wherein steps (a) and (b) comprise the step of operating a receive beamformer in a multiple simultaneous receive beam mode.

44. In an ultrasonic imaging system for simultaneously displaying both fundamental and harmonic frequency information, said system comprising:
   a first processor operative to generate fundamental frequency intensity values;
   a second processor operative to generate harmonic frequency intensity values;
   an image plane memory operative to store said intensity values;
   a mapping device coupled to the image plane memory for generating individual display indicia as a function of both the fundamental and harmonic frequency intensity values; and
   a display responsive to the display indicia.

45. The invention of claim 44 wherein the image plane memory includes a fundamental and a harmonic image plane memory operative to store the fundamental and harmonic frequency intensity values, respectively.

46. The invention of claim 44 wherein the mapping device is adapted to determine intensities of the display indicia as a function of the fundamental frequency intensity values.

47. The invention of claim 44 wherein the mapping device is adapted to determine color of the display indicia as a function of the harmonic frequency intensity values.

48. The invention of claim 44 wherein the mapping device is adapted to determine the display indicia as a function of a ratio of fundamental and harmonic frequency intensity values.

49. The invention of claim 44 wherein the first processor comprises a Doppler processor.

50. The invention of claim 44 wherein the second processor comprises a Doppler processor.

51. The invention of claim 44 wherein the mapping device comprises a look-up table.

52. The invention of claim 54 wherein the first and second processors comprise means for interleaving the respective intensity values on a scan line-by-scan line basis, and wherein the display indicia are representative of at least a portion of the imaged region associated with a plurality of lines.

53. The invention of claim 44 wherein the first and second processors comprise means for interleaving the respective intensity values on a plurality-of-scan lines by plurality-of-scan lines basis.

54. In a method for ultrasonically imaging a target comprising the step of transmitting ultrasonic energy into a tissue at a fundamental frequency, the improvement comprising:

(a) generating a harmonic frequency information signal in response to reflections from the tissue;

(b) generating a fundamental frequency information signal in response to reflections from the tissue;

(c) combining the harmonic frequency information signal and the fundamental frequency information signal through a mapping function to form individual display indicia of an imaging signal for display.

55. The method of claim 54 wherein both the fundamental and harmonic frequency information signals are generated by a B-mode processor.

56. The method of claim 54 wherein the fundamental frequency information signal is generated by a motion processor with no clutter filtering.

57. The method of claim 54 wherein the harmonic frequency information signal is generated by a motion processor with no clutter filtering.

58. The method of claim 52 wherein the harmonic information signal is generated by a Doppler processor.

59. The invention of claim 15 wherein the generator generates the display indicia representative of two-dimensional representation of the imaged region.

60. A method for ultrasonically imaging a target comprising the following steps:

(a) applying energy at fundamental frequencies to a transducer;

(b) acquiring harmonic signals responsive to harmonic frequencies different than the fundamental frequencies;

(c) acquiring fundamental signals responsive to the fundamental frequencies;

(d) combining the harmonic and fundamental signals to form individual display indicia of an output signal; and (e) generating an image responsive to step (d).

61. In a method for ultrasonically imaging a target comprising the step of transmitting ultrasonic energy into a tissue at a fundamental frequency, the improvement comprising:

(a) isolating harmonic information and fundamental information from reflections from the tissue;

(b) processing harmonic signals responsive to the harmonic information;

(c) processing fundamental signals responsive to the fundamental information;

(d) combining the harmonic and fundamental signals to form individual display indicia of an output signal; and (e) generating an image responsive to step (d).

62. The method of claim 60 or 61 wherein step (d) comprises the step of applying the harmonic and fundamental signals to a look-up table.

63. The method of claim 60 or 61 wherein the harmonic and fundamental signals comprise detected signals.

64. The method of claim 60 or 61 wherein step (d) occurs prior to scan conversion.

65. The method of claim 60 or 61 wherein the harmonic and fundamental signals are sequentially acquired.

66. The method of claim 60 or 61 wherein the harmonic and fundamental signals are simultaneously acquired.

67. The method of claim 60 or 61 wherein step (e) comprises the step of generating the image in a portion of a scan region.

68. The method of claim 60 or 61 wherein step (e) comprises the step of generating the image for each point in a scanned region.

* * * * *

UNITED STATES PATENT AND TRADEMARK OFFICE
CERTIFICATE OF CORRECTION

PATENT NO. : 5,961,460  
APPLICATION NO. : 08/838920  
DATED : October 5, 1999  
INVENTOR(S) : Guracar et al.

Page 1 of 1

It is certified that error appears in the above-identified patent and that said Letters Patent is hereby corrected as shown below:

<u>On the Title Page</u>

Column 2, line 14, please change "Arerkiou" to --Averkiou-- .

Column 2, line 2, under "OTHER PUBLICATIONS", please change "Buffles" to --Bubbles-- .

Column 2, line 5, under "OTHER PUBLICATIONS", please change "Transit" to --Transmit-- .

Column 6, line 1, please change " $\tilde{C}^{RGB}$ " to -- $\vec{C}^{RGB}$ -- (in the equation) .

Column 7, line 29, please change "signal $1_0$" to --signal $I_D$-- .

Claim 31, line 1, please change "28" to --30-- .

Claim 52, line 1, please change "54" to --44-- .

Claim 58, line 1, please change "52" to --54-- .

Signed and Sealed this

Thirtieth Day of January, 2007

JON W. DUDAS  
*Director of the United States Patent and Trademark Office*